US00PP12452P2

(12) United States Plant Patent
Stemkens

(10) Patent No.: US PP12,452 P2
(45) Date of Patent: Mar. 12, 2002

(54) VERBENA PLANT NAMED 'SPIKENA'

(75) Inventor: Henricus G. W. Stemkens, Hoorn (NL)

(73) Assignee: Novartis Seed B.V., Enkhuisen (NL)

( * ) Notice: Subject to any disclaimer, the term of this patent is extended or adjusted under 35 U.S.C. 154(b) by 39 days.

(21) Appl. No.: 09/615,196

(22) Filed: Jul. 13, 2000

(51) Int. Cl.[7] ..... A01H 5/00
(52) U.S. Cl. ..... Plt./308
(58) Field of Search ..... Plt./308

(56) References Cited

PUBLICATIONS

UPOV–ROM GTITM Computer Database 2001/02, Apr. 2, 2001, GTI Jouve Retrieval Software, Citation for Verbena 'Spikena'.*

* cited by examiner

*Primary Examiner*—Bruce R. Campell
*Assistant Examiner*—June Hwu
(74) *Attorney, Agent, or Firm*—Bruce Vrana

(57) ABSTRACT

A new Verbena plant particulary distinguished by its large violet blue flower, early flowering, and a spreading habit.

1 Drawing Sheet

BACKGROUND OF THE NEW PLANT

The present invention comprises a new distinct cultivar of Verbena, botanically known as *Verbena×hybrida*. The new cultivar is propagated from cuttings resulting from the cross of 'W711' and 'W681'. 'W711' is a lavender flowering Verbena having a spreading habit. 'W711' is not commercially available and is not known by any synonyms. 'W681' is a purple flowering Verbena having a spreading habit. 'W681' is not commercially available and is not known by any synonyms. Neither 'W711' or 'W681' has been patented. As a result of this cross the present cultivar was created in 1996 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new Verbena plant is an annual in most climatical zones in the US, only in zones 9 and 10 it is a perennial plant.

DESCRIPTION OF THE DRAWING

This new Verbena plant is illustrated by the accompanying photographic drawings which show blooms, buds and foliage of the plant in full color, the color shown being as true as can be resonably obtained by conventional photographic procedures.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on 14 weeks old plants, blossmed under natural light in a greenhouse. Color readings were taken in the greenhouse under ambient light. Color references are primarily to The R.H.S. Color Chart of The Royal Horticultural Society of London.

Differences between the new variety 'Spikena', its parents and a similar cultivar

| Character | 'Spikena' | 'W711' | 'W681' | 'Temari Violet' (P.P. No. 10,801) |
|---|---|---|---|---|
| Flower color | violet blue | lavender | purple | purple |
| Seed set | no | no | yes | yes |
| Flower size | 17–20 mm | 18–20 mm | 12–14 mm | 20–23 mm |

The Plant

Classification — Botanical: *Verbena×hybrida.*
Parentage:
*Female parent.*—A seedling named 'W711' is one of our seedlings from our W-generation of plants bred in 1992.
*Pollen parent.*—A seedling named 'W681' is one of our seedlings from our W-generation of plants bred in 1992.
Growth habit: Spreading.
Plant height: 20–25 cm.
Spreading area of plant: 80–120 cm.
Growth rate: Very vigorous.
Strength: Good.
Branching character: Freely branching and lateral branching at every node.
Blooming period: From April until November.

The stem

Diameter: 2–3 mm.
Shape: Tetragonal.
Anthocyan pigmentation: Absent.
Color: RHS 141A.
Length of internode: 30–70 mm, depending on the light where the plant is propagated.
Pubescence: A light pubescence is present.

The Foliage

Phyllotaxis: Opposite.
Shape of blade: Broadly ovate.

Texture:
*Upper side.*—Slightly pubescent.
*Lower side.*—Slightly pubescent.
Venation: Pinnate.
Leaf margin: Biserrate and irregularly incised.
Leaf base: Truncate.
Leaf apex: Acuminate.
Length: 35–50 mm.
Width: 26–38 mm.
Depth of incision: 2–3 mm.
Color:
*Upper side.*—Medium green 141A.
*Lower side.*—Light green 138A.
Pubescence: Some pubescence is present.
Length of leaf stem: 5–10 mm.

The Bud

Peduncle length: 40–60 mm, depending on season.
Size:
*Diameter.*—2 mm.
*Length.*—8–12 mm.
Shape: Elongated and ovate. Color: Medium green 137C.
Sepals:
*Color.*—Green 137D.
*Form.*—Upright.
*Number.*—5, fused.
*Size.*—8 mm.
*Shape.*—Elongated.

The Flower

Direction: Ascending.
Diameter: 17–20 mm.
Height: 18–22 mm.
Borne: In a cluster.
Form: Salverform, sessile on terminal spikes.
Cluster: Spike.
Color: Violet 83A, turning 84C as flower matures.
Eye: A very small green-white (157C) eye is present. The three lower petals exhibit this green-white coloration at their bases. The center of the of the flower if very dark, 79B.
Overlapping of petals: Separate.
No. of petals: 5.
Shape of the petals: Gamopetalos, grown together at the base of the petal. Each petal is heart shaped at the apex.
Size of the petal:
*Length.*—6–9 mm.
*Width.*—5–7 mm.
Spike:
*Length.*—25–45 mm.
*Diameter.*—40–60 mm.
Calyx: Length of 10–12 mm and slightly pubescent.
Anthocyan pigmentation of calyx limb: Absent.
No. of flowers per spike: 20–35.
Fragrance: A very soft rosy-sweet fragrance.
Lastingness of the bloom: New florets continue to open in one spike over a period of 18 days.

Reproductive organs

One pistil and 5 stamens: color for both is 150D. The stamen size is 16–19 mm in length. The pistil size is 14–16 mm in length. Pollen is present with a color of 5D. The filaments and anthers are fused to the corolla. The anthers are enclosed and not a prominent feature of the flower. 'Spikena' does not freely seed set.

Roots

Type of roots: Fibrous. Roots start to grow on every part of the stem that contacts the soil, so not only at the nodes.

Physiological and ecological characteristics

Good tolerance to heat and cold. Strong resistance to pests and diseases, particularly powdery mildew.

What is claimed is:

1. A new and disinct variety of Verbena plant, substantially as herein illustrated and described, characterized particularly as to novelty by larger violet blue flowers than other Verbena plants, which appear earlier on the plant, and a growing habit that is spreading and very vigorous.

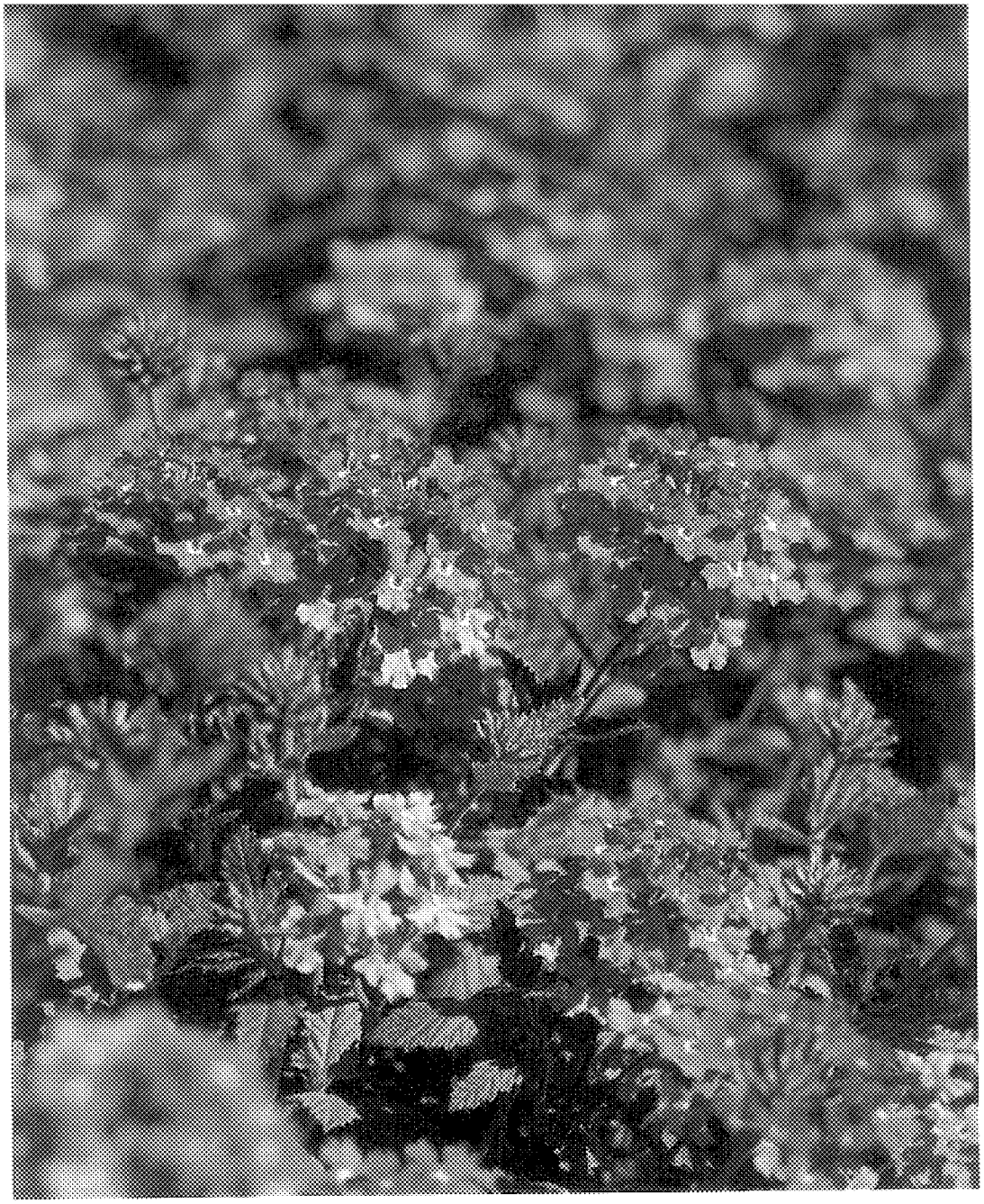

* * * * *